United States Patent
Adekenov (12)

(10) Patent No.: US 6,242,617 B1
(45) Date of Patent: Jun. 5, 2001

(54) METHOD AND DEVICE FOR PRODUCTION OF LYOPHILIZED HYDROCHLORIDE-1β, 10β-EPOXY-13-DIMETHYLAMINO-GUAIA-3 (4)-EN-6,12-OLIDE

(76) Inventor: Sergazy Mynzhasarovich Adekenov, 21 Michurin Street Bldg. 1, Apt. 6, Karaganda 470060 (RU)

( * ) Notice: Subject to any disclaimer, the term of this patent is extended or adjusted under 35 U.S.C. 154(b) by 0 days.

(21) Appl. No.: 09/331,491

(22) PCT Filed: Dec. 19, 1997

(86) PCT No.: PCT/KZ97/00006

§ 371 Date: Jul. 29, 1999

§ 102(e) Date: Jul. 29, 1999

(87) PCT Pub. No.: WO98/28303

PCT Pub. Date: Jul. 2, 1998

(51) Int. Cl.$^7$ ............................ C07D 307/33; B01D 33/00

(52) U.S. Cl. ............................................ 549/298; 210/364

(58) Field of Search ............................. 549/298; 210/364

(56) References Cited

PUBLICATIONS

J. March., "Advanced Organic Chemistry—Reactions, Mechanisms, and Structure", 3$^{rd}$ ed., John Wiley & Sons, New York, 1985.*
Chemical Abstract 126 : 263418v, 1997.*
Chemical Abstract 98: 86229q, 1983.*

\* cited by examiner

*Primary Examiner*—Ba K. Trinh
(74) *Attorney, Agent, or Firm*—Rader, Fishman & Grauer PLLC

(57) ABSTRACT

Method of producing an antitumor preparation of natural origin lyophilized arglabin 1β, 10β-epoxy-13-dimethylamino-guaia-3(4)-en-6, 12-olide hydrochloride includes resin extraction from a natural material, its purification from worthless substances, resin separation into separate components by column chromatography with production of technical arglabin. Technical arglabin further undergoes recrystallization, amination and hydrochloration at given parameters of pH solutions with production of aminoarglabin hydrochloride and its further lyophilization and high quality identification by IR-spectroscopy. A device for the realization of the method is also disclosed herein.

5 Claims, 2 Drawing Sheets

Figure 1:
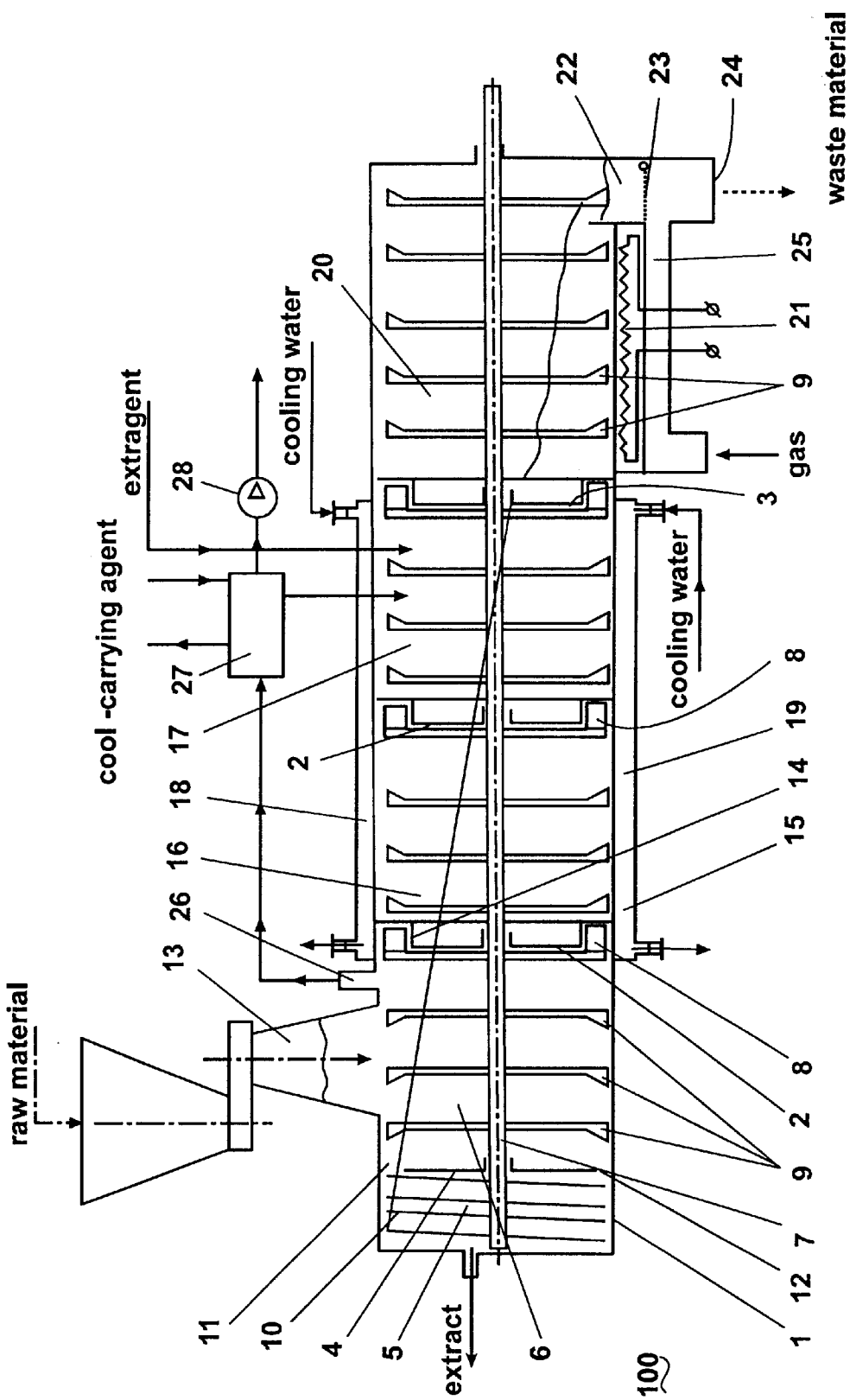

METHOD AND DEVICE FOR PRODUCTION OF LYOPHILIZED HYDROCHLORIDE-1β, 10β-EPOXY-13-DIMETHYLAMINO-GUAIA-3(4)-EN-6,12-OLIDE

This application is a 371 of PCT/KZ97/00006 dated Dec. 19, 1997.

The present invention relates to pharmaceutical industry, to the sesquiterpene lactones and, particularly, to the method of production of lyophilized hydrochloride 1β, 10β-epoxy-13-dimethylamino-guaia-3(4)-en-6,12-olide of the following formula

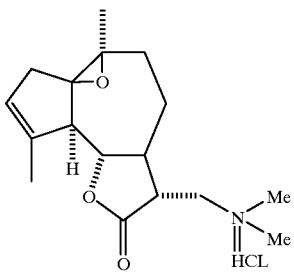

(I)

which has antitumour activity and can be used to develop new preparations for chemotherapy of malignant tumours.

The method of production of arglabin lyophilized having antitumour activity from the natural material-flower baskets and leaves of endemic plant *Artemisia glabella Kar. et Kir.* was described in preliminary patent of the Republic of Kazakstan, N 5277, cl.CO7D 307/93, A61K, 31/365, 1997).

According to this method initially dry grinded natural material is treated by a solvent in the extractor, then extracted substances (resin) are purified from worthless products through treatment by 60% acqueous solution of ethyl alcohol. The resin produced at the stage of purification is divided into separate components by the method of column chromatography on silicogel. The said column is eluted with benzene and the fractions containing arglabin are separated. Benzene is distilled and technical arglabin is produced which is further subjected to crystallisation, amination and hydrochloration. In this method amination is carried out by dimethylamine with production of a solution containing arglabin. Then the alcohol solution of aminoarglabin is barbotaged by chlorine hydride and the target product—aminoarglabin hydrochloride is produced. Amination and hydrochloration reactions are controlled by the methods of thin layer chromotography. Technical hydrochloride of aminoarglabin is purified by crystallization with subsequent drying and lyophilization.

Disadvantages of the above method are its rather low yield of target products in the amination and hydrochloration reactions.

Different devices are used for extraction, for example, the device consisting of extractor with a jacket in the extraction zone, evaporator, condenser and heater (the USSR author's certificate N 1117071, cl. BO1D 11/02, 1984).

The USSR author's certificate N 670310, cl. BO1D 11/02, 1979 describes the device for gas-liquid extraction consisting of evaporator, condenser and extractor, where the extracted mixture is heated by the heat produced at condensation of extragent vapours transported from evaporator, said heat is transmitted through the wall of the extractor.

The disadvantage of all these devices is periodicity of their operation what cannot provide high productivity. These devices also do not provide extraction of the extragent from waste material what results in great losses of the extragent. In the USSR author's certificate N 1117071 reacting mixture is heated by an additional power supply what increases power consumption in the process of extract production.

The USSR author's certificate N 1426611, cl. BO1D 11/00, 1988 describes the device for extraction in the solid-liquid system consisting of the body, extraction chamber with changeable container, evaporator and condenser which enables to distill the extragent from the solid phase by a warm inert gas at the final stage of extraction. This device also does not provide continuous operation and, respectively, has low productivity. Besides, when volatile extragents are distilled by a warm gas while condenser is cooled by the water, the whole extragent can be taken away with the gas without its condensation in the condenser. For example, according to our calculations, to distill chloroform by a gas with initial temperature 70° C. and to cool it in the condenser to 20° C., 5 m$^3$ of gas are required for evaporation of 1 kg of chloroform and for its condensation partial pressure of chloroform in the gas must be not lower than the saturation partial pressure at 20° C. what corresponds to the content of 1 kg of chloroform in 1 m$^3$ of gas. Thus, partial pressure of chloroform in the gas in the above example is 5 times lower than that required for condensation, i.e. no condensation is possible in the condenser and all the chloroform will leave the condenser together with the gas.

There are also some special devices for solvent removal from the waste material, for example, the method and device for removal of the solvent from solid substances, consisting of a capacity for waste material contact with heat-carrying agent, separators for extragent and heat-carrying agent separation, condensers for extragent vapours. (Patent EPV N00356338, cl. BO1D 11/00, 1990).

Such devices are complicated and energy consuming, besides, when waste material is reloaded from the extraction device to other devices, it is impossible to prevent extragent losses or it is necessary to use complex hermetic devices for reloading.

The closest to the claimed device is a section blade extractor of dry natural material of continuous operation consisting of cylindric body divided by partitions with openings into not less than three sections, separation and humidity chamber, shaft mounted on the same axis with the body with reloading ladles, mixing blades and loader are attached to said shaft (the USSR author's certificate N 1627208, cl. BO1D 11/02, 1991).

This design provides increase in productivity as compared with the above devices but this increase is not sufficient. The disadvantage of this design is also high extragent consumption as this device does not enable to extract extragent from waste material what results in extragent losses. The usage of other known devices to extract extragent from waste material considerably increases the cost of the installation and requires additional devices providing reloading and transportation of wet waste raw material without extragent emission to the environment.

The purpose of the present invention is to develop a method and device which could provide high yield of target product, complete extraction of the extract from raw material, increase in productivity of the extraction device, reduction of power supply, minimization of extragent losses, exclusion of extragent emission in the environment and, thus, guarantee of environmentally safe production.

According to the invention these tasks are solved by claims 1 and 3 of the claims. Preferred embodiments of the invention are given in dependent claims.

The method of production of lyophilized hydrochloride 1β, 10β-epoxy-13-dimethylamino-guaia-3(4)-en-6,12-olide-antitumour preparation arglabin lyophilized from endemic plant *Artemisia glabella Kar.et Kir.* comprises resin extraction from raw material, its purification from worthless side substances, separation of said resin into separate components by column chromatography with production of technical Arglabin which is further subjected to recrystallization, amination and hydrochloration with production of aminoarglabin hydrochloride and its further recrystallization, drying, lyophilization and high quality identification, where preferred amination is carried out by solution of crystallic arglabin in alcohol with addition of dimethylamine in said alcohol solution till pH of the solution reaches 12.3–12.4, and where to extract aminoarglabin hydrochloride from said solution containing aminoarglabin alcohol is distilled and chloroform is filled in, the remaining water is removed, said solution is filtered said chloroform is evaporated and alcohol added, then the solution is barbotaged by chlorine hydrine to 5.0–5.5 pH solution, alcohol is evaporated and ethylathetate added.

It is preferable to carry out high quality identification of arglabin by IR-spectroscopy.

In the claimed method stages of amination and hydrochloration under given operation parameters of pH-solutions provide high yield of 13-dimethylaminoalglabin and 13-dimethylaminoalglabin hydrochloride reactions. In its turn, it provides high output of target product.

The invention also includes the device to implement this method. Technical result of the present invention is achieved by the device for lyophilized arglabin extraction from natural raw material consisting of horizontal extractor including cylindrical body divided by partitions with openings into not less than three sections, separation and humidity chambers, shaft mounted on the same axis with the body with reloading ladles, blade mixers and the loader attached to it, the said extractor is provided with additional section with heated walls to remove extract from waste material and dry waste material collector, the walls of contact sections are water-cooled, cavities of cooling jackets of upper parts of the walls of said section being in contact with vapour-gas medium and lower parts of the walls being in contact with extraction mixture are not connected with each other, the system of gas circulation is connected to the extractor cavity, the said system consists of branch pipe for gas supply connected to dry waste material collector, branch pipe for gas removal connected to the cavity of the contact section of the extractor, low temperature condenser and ventilator, lead screw mounted in the separation chamber is connected to said shaft of the extractor and the partition between the separation and the humidity chambers is supplied with additional opening in its upper part.

According to one claim of the invention, the cylindrical body of the extractor is mounted with an inclination.

The other claim of the invention is that the branch pipe for the extract removal from the separation chamber of the extractor is connected to the filtering centrifuge connected in series with evaporator and condenser.

The advantage of the invention is that as compared with the known devices the present design provides heating of extracted mixture and keeping of its temperature at a required level due to condensation of extragent vapour inside the extractor and usage of condensation heat for heating of extracted mixture what results in increase in the productivity of extraction and reduction in extragent consumption and power supply.

The device contains preferred additional section with heated walls designed to remove extragent from waste material what enables to reduce extragent losses.

The device is supplied with the system for gas circulation which removes the air entering the extractor in the pores of raw material, and, thus, prevents emission of extragent vapours into atmosphere and excludes extragent losses, as well as removes air or other gas supplied to replace extragent vapour in dry waste material pores before its unloading what also reduces extragent losses.

The device provides continuous removal of not only precipitated but also of suspended particles from the separation chamber after purification of the extract before its withdrawal from the extractor.

The preferred technology provides environmentally safe operation of the device without extragent emission in the environment and deep gases precipitation from the extractor before their emission to the atmosphere.

The present extractor provides continuous process of multi-stage extraction of final product by liquid extragent with continuous mixing of extraction mixture at optimal extraction temperature and counterflow of raw material and extragent that ensures the most complete extraction of the final product out of raw material and maximal productivity without extragent losses. Below the invention is explained in details on the examples of its implementation.

Figure 2:
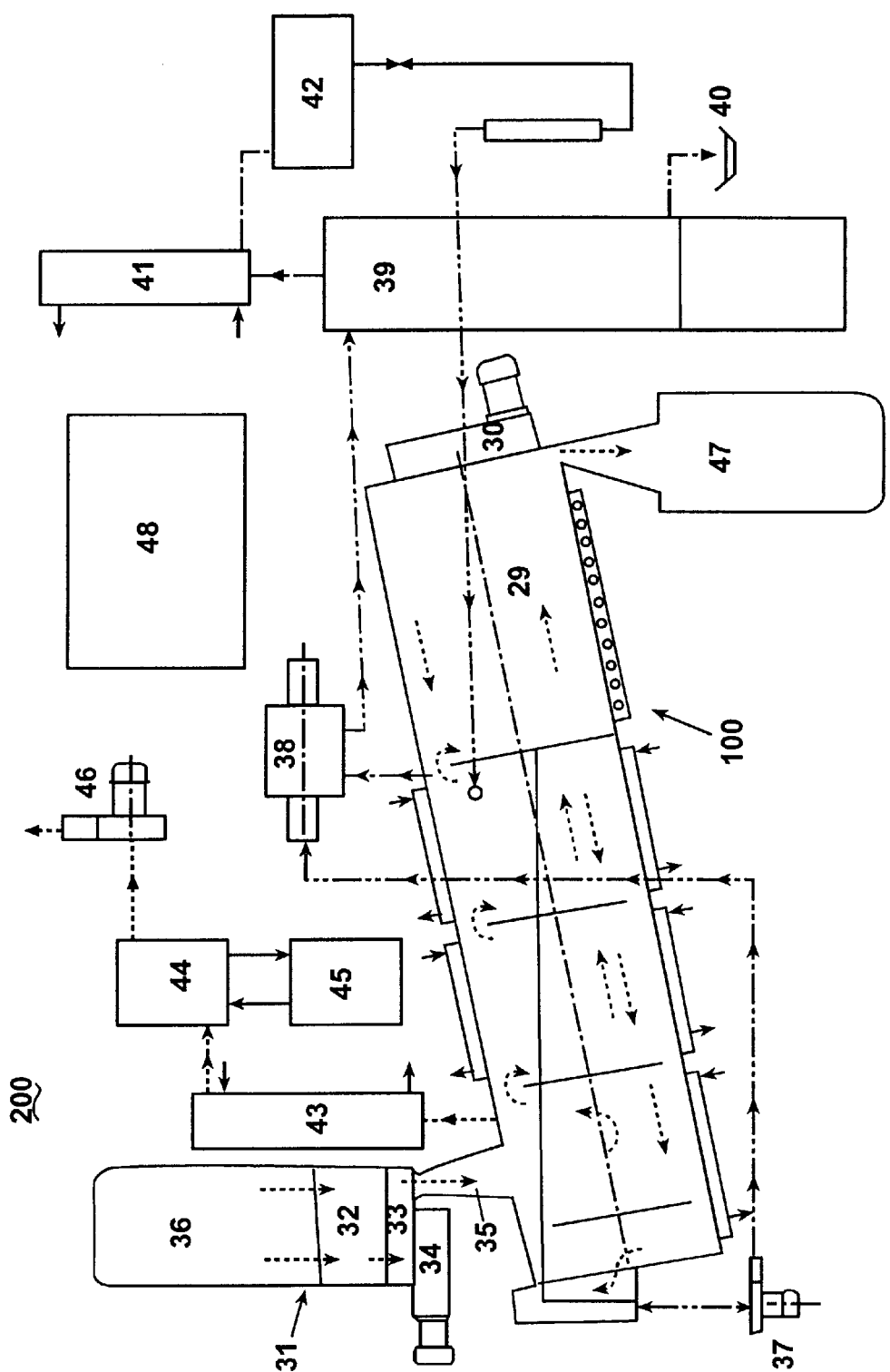

FIG. 1 shows the extractor, its longitudinal section. FIG. 2 shows the scheme of the device for the extraction of arglabin lyophilized from raw material.

The extractor consists of a cylindric inclined body 1 divided by vertical partitions 2 and 3 into sections. Partition 4 divides the first section into separation 5 and humidity 6 chambers. Along the axis of the body, the rotating shaft 7 is mounted, reloading ladles 8 and blade mixers 9 are attached to it. In separation chamber 5 (sedimentator) peripheral lead screw with a small gap to the body is placed, its internal edge in the upper point of the extractor is dipped into liquid. In the upper part of the partition 4 the opening 11 is made, its lower edge is located at the liquid level. There is also the opening 12 in the lower part of partition 4. The loading device 13 with feeder and bin for raw materials is mounted on the humidity chamber 6 in the first section of the extractor. There are two openings 7 in the partitions 2, the upper opening 14 is intended for reloading of raw material to the next section and the lower opening 15 closed by mesh is designed for extragent transfer.

There can be one or several contact sections 16 in the extractor. In the last section with respect to raw material motion, contact section 17, there is no opening in the partition 3 and said partition 3 is hermetically sealed in the part which is lower than the level of extraction mixture.

On the body 1 of the extractor near contact sections 16, 17, water jackets 18 and 19 are made. Water jacket 18 is placed higher than the extracted mixture level in the extractor and water jacket 19 is placed lower than that level. The cavities of both jackets are not connected with each other and have separate branch pipes for supply and discharge of cooling water.

Next to the last contact section 17 along the raw material motion, there is an additional section 20 (dryer) designed to remove extragent from the waste raw material. On the body of section 20, predominantly in its lower part being in contact with the waste material, the heater 21, for example, an electric heater, is mounted. In section 20 the collector of dry waste material 22 is placed, it is supplied with a hinged out window 23 with a grid, the unloading port of collector 22 is closed by easily removed lid 24. The canal 25 is designed to supply air or inert gas to ventilate waste material in the collector 22. The gas is heated, for example, by heater 21 or a special gas heater. In the upper point of the body 1 near the contact section 16 there is the branch pipe 26 for gas removal from the extractor, the said branch pipe is connected with low temperature condenser 27 cooled by the coolant supplied by the refrigerator. The ventilator 28 is designed to draw off the gases.

The extractor operates as follows:

Dry grinded natural raw material (flower baskets and leaves of *Artemisia glabella Kar.et Kir.*) is supplied through the feeder 16 into the humidity chamber 6, where it is mixed with extragent by mixers 9. The raw material impregnated with extragent is reloaded by reloading ladles 8 through the port 14 in partitions 2 into contact section 16 where it is continuously mixed with extragent by mixers 9 and moved to the next section. Further the raw material is transported by reloading ladles 8 to the section 17 into which the newly made extragent is supplied from the opposite side. In the section 17 the raw material is washed by a newly made solvent, released from the residue of the target product and by reloading ladles is transported to the section 20 where the extragent is evaporated from waste material during its contact with hot walls. Mixers 9 are used to mix the waste material and to achieve uniform drying and to transport it to waste material collector 22 where the extragent vapour is displaced from the pores of waste material by heated air or inert gas supplied under the grid 23. As the collector 22 is filled, the dry ventilated waste material is discharged, to do this the grid 23 is lowered and the lid 21 is opened. The extragent vapour flows through the upper opening in partition 4 from the drying section 20 to the section 17 where the most part of said vapour is condensed on the surfaces cooled by water passing through the upper water jacket 18 as well as on the surface of extracted mixture heating it. Condensed extragent flows down to the extracted extragent mixture. The residue of extragent vapour together with the air flows through the upper opening in the partition into the contact section 16 where they are condensed to partial saturation pressure corresponding to the temperature of the vapour—gas mixture drawn off from the extractor. The temperature of the extracted mixture is regulated by the amount of cooling water supplied to the lower water jacket 19. Gases from the extractor containing a small amount of extragent vapours are transported through the branch pipe 26 to the low temperature condenser 27 cooled by the coolant from a refrigerator machine, in the said condensor extragent vapours are almost completely condensed from gases. The condensate from the condenser 27 is returned to the extractor. The gas cleared from extragent vapours is emitted through the discharge ventilator 28 to the atmosphere. The air entering the extractor with the raw material in its pores is drawn off in the same way through the branch pipe 26.

The newly made extragent enters section 17 near the unloader of waste material, the condensed extragent from the drying section 20 runs down to the same place. The extragent in the reactor moves from section to section through the lower openings 15 in the partitions in the opposite direction to the raw material flow. Grids on these openings prevent opposite motion of raw material. From the humidity chamber 6 the extragent through the lower opening in the partition 4 enters the separation chamber 5 where it is purified, heavy particles go down and light particles rise up and are removed by the peripheral lead screw from the separation chamber to the humidity chamber, suspended particles are removed through the upper opening 11 and precipitated particles are removed through the lower opening 12. Purified extract (extragent saturated with extracted substances) is transported from the near-axis zone of the extractor for the further processing as it is shown in FIG. 2.

According to the scheme given in FIG. 2 the extraction device consists of continuously operating counterflow section extractor 1 with additional section 2 with heated walls for extragent removal from waste material with common drive 3. The loader consisting of intermediate bunker 4, feeder 5 with drive 6 and canal 7 is mounted on the extractor. The changed capacity 8 with raw material is placed on the intermediate bunker 4, a standard craft-sack is used as changed capacity. The pump 9 is intended to feed the extract from the extractor 1 to the filtering centrifuge 10 placed on the extractor where the extract is cleared from suspended particles. Particles precipitated from the extract in the centrifuge are discharged from the centrifuge to the last stage of the extractor. Then the extract is feeded to the film-type evaporator 11 with built-in steam generator for condensation. The condensed extract is periodically poured out from the condenser 11 to the changeable capacities 12. The evaporator 11 is connected with the water-cooled condenser 13 from which the distilled extragent is transported to the buffer tank 19. Pure extragent is transported from the tank 19 to the last stage of the extractor and moved to the first stage in the direction opposite to that of the raw material flow, extracting target substances from it. The tank 19 is equipped with level meter, flow meter and regulator of extragent and flow.

The extractor 1 is equipped with the system for gas removal which consists of condenser 14 cooled by water, freezer 15 which simultaneously serves as an evaporator for freon refrigerator machine, in the capacity of which the freezer of a household fridge is used, and ventillator 17. Gases from the extractor are transported to the condenser where the excess of extragent vapours, not having condensed on the walls of the extractor, is condensed. Further, the gases enter the freezer 15, the temperature of its walls is kept at −15−20° C. by the refrigerator machine 16, and the extragent vapours remained in gases condense on its walls. Then gases practically completely cleared from extragent vapours are discharged by the ventilator 17 to the common ventilation system in the building.

The worked out and dried raw material is collected into easily removed changeable capacity 18 (a standard craff-sack).

Instruments for direction, control, regulation, signalling and protection of the device are mounted on the control panel 20. All units of the device operate under low pressure what excludes penetration of the vapour into the premises.

The device is mounted on its own frame and does not need special basement. Its operation is attended by 1–2 specially trained operators.

The design of the device enables without its dismounting to completely clean the device from the extragent without losses into the environment and almost completely (95–98%) from raw material when the device is prepared for repairings or change of raw material or extragent.

The design of the device enables to observe its operation and readjust it without unloading of raw material or extragent and without extragent emission to the environment.

During working day 0.539 kg of resin (the total amount of extracted substances) is produced what amounts to 7% with respect to dry raw material. The resin produced is further transported to stage II where it is purified from side substances.

For this purpose the resin is treated by 1.078 liter of ethyl alcohol heated to 60° C., the resin is solved in the said alcohol under mixing. Then heated distilled water is poured in the volume ratio of ethyl alcohol to water equal to 2:1.

The mixture is mixed carefully during 30 minutes and kept at room temperature without mixing during 24 hours. Side substances precipitate during this time. In a 24-hour period the sedimentation is mixed by the mixer and alcohol-water solution is filtered by vacuum. Alcohol as an azeothropic mixture with water containing 68–70% of alcohol is distilled from the obtained filtered substance under vacuum and at temperature of 50–52° C. The yield of resin amounts to 286 g.

In stage III the resin produced in stage II is divided into individual components by column chromatography. Benzene is fed under pressure in the column and benzene fraction containing arglabin is separated. The presence of arglabin in the benzene fraction is determined by the method of thin layer chromatography on Silufol plates. After benzene distilling from fractions, there remains technical arglabin with an admixture of yellow oil amounting to 33.1 g what equals to 11.7% of the processed resin.

Stage IV is a process of arglabin recrystallization. For this, technical arglabin is dissolved in hexane while heating on water bath at the ratio of product (kg)-solvent (1) equal to 1:10 and filtered under vacuum. During cooling to room temperature the crystals of arglabin start to isolate from the filtrate. After complete hexane removal, arglabin yield amounts to 21 g (63%).

At stages V and VI arglabin is aminated and hydrochlorated. To produce aminoarglabin, crystallic arglabin is dissolved in alcohol. Then dimethylamine is added to the alcohol solution till bringing pH to 12.3–12.4. Then alcohol is distilled from the solution containing aminoarglabin and chloroform is poured in. The main part of the water is separated by separating funnel. Traces of the remaining water are removed by one of the dryers ($MgSO_4$ or $Na_2SO_4$) till total transparency is achieved, the duration of treatment is about 12–14 hours. The solution is filtered, chloroform is evaporated and alcohol is added. Then said solution is barbotaged by chlorine hydride till pH reaches 5.0–5.5. Alcohol is evaporated from the solution and ethylacetate is added. The crystals of 13-dimethylaminoarglabin hydrocholide are precipitated. Its yield is 105%. The solution is evaporated till dry and technical aminoarglabin hydrochloride in the form of a powder is produced.

At stage VII aminoarglabin hydrochloride (technical product) is purified by fractional recrystallization. The product is dissolved in chloroform, then said chloroform is removed on rotatory evaporator. Under intensive stirring ethylacetate is added to the remained resin. The precipitated sedimentary of aminoarglabin hydrochloride is filtered through vacuum-pistol and used for the production of arglabin-lyophilized preparation. The yield of arglabin-lyophilized (target product) is 20 g (95% at this stage).

At the last stage VIII the produced target product is dried over anhidrone under vacuum, dissolved with apyretic distilled water at ratio: 2 g of dry substance per 100 ml of water. The produced solution is lyophilized by one of the following methods.

Method 1. Produced aqueous solution is passed through cotton-gauze tampon in the tank with Millipor filter. The solution is filtered through sterile Millipor trimmed by filtering plates into a sterile glass vessel. Then the solution is pumped by means of vacuum from the glass vessel into a measuring burette from which it is poured into 2 ml bottles and dried in lyophilizer KS-30. To do this the bottles are placed on trays. When the trays are filled with bottles, they are wrapped into a sterile sheet and placed on freezing counter for hardening at −40° C. for not less than 24 hours. After this procedure drying is commenced. In 2 hours after the beginning of drying, heating of the shelves is turned on. The shelves are heated gradually up to +50±5° C. The product turns from negative to positive temperature at 12th–13th hour of drying. The final temperature of the product should not exceed +60° C.

Duration of drying is 24 hours. After the lyophilic drying, the bottles with preparation are immediately closed by the corks, covered by caps and rolled. Each bottle contains 0.04 g (0.00004 kg) of preparation.

Method 2. Aqueous solution is filtered through cotton-gauze tampon or 8 layers of gauze, poured into 2 ml bottles or ampules and lyophilized under the above conditions. The bottles with dry preparation are immediately closed by the corks, covered with caps and rolled. Ampules are soldered. Bottles or ampules with preparation are packed up in bicks or double-layered sacks and sterilized in autoclave during 20 minutes at the pressure of 1.2 Atm and temperature 120° C. Each bottle (ampula) contains 0.4 g (0.00004 kg) of the preparation.

Method 3. Prepared aqueous solution is filtered through cotton-gauze tampon or 8 gauze layers, poured by 200 ml into flasks of volume of 500 ml, closed by cotton-gauze tampons and tied up by oil-paper. The flasks with solution are sterilized in autoclave during 30 minutes at 1.2 Atm and the temperature of 120° C. The sterile solution is cooled to room temperature, sterily poured by 2 ml into the bottles with the volume of 10 ml and dried in the lyophilizer as stated above. After lyophilization, each bottle contains 0.04 (0.00004 kg) of preparation.

The yield of preparation is 17 g what amounts to 88.2% at this stage and 0.22% with respect to air-dry natural material. Arglabin lyophylized preparation is a straw-white compound with a bitter taste.

According to the present invention high qualitative identification of arglabin lyophilized is made by IR-spectroscopy. Spectrum of 1% of standard arglabin sample solution in chloroform is analysed by IR-spectrometer. The spectrum has characteristic absorption lines at 2800, 1775, 1650 $cm^{-1}$.

The 1775 $cm^{-1}$ line is characteristic for carbonyl group of γ-lactone and it does not overlap with other spectrum lines, therefore it is used to calculate the coefficient of absorption for the solution of a standard arglabin sample.

The coefficient of absorption is calculated by the formula:

$$a = \frac{A}{c_1 \cdot c_2 \cdot b}$$

where A is an optical density;
$c_1$ is a fraction of investigated compound in the sample; %
$c_2$ is sample concentration in the analysed solution, %;
b is the thickness of cuvette, mm.

Content of arglabin in the standard sample is equal to 100%. Concentration of the sample in the analysed solution is 1%, cuvette thickness is 0.4 mm.

$$a = \frac{0.9852}{(1) \cdot (100) \cdot 0.4} = 0.02463$$

To make quantitative estimation, IR-spectrum of arglabin solution in chloroform with known concentration is measured. The band width of T % at 1775 $cm^{-1}$ is transformed into optical density and arglabin concentration is calculated by the formula:

$$C_2 = \frac{A}{a \cdot b \cdot c_1}$$

Percentage concentration of arglabin is determined by spectrophotometer and it is not less than 99.9%.

The control of the quality of preparation can also be made by the method of thin layer chromatography, qualitative reaction of preparation interaction with solution in sulphuric acid, determination of melting temperature, specific rotation.

Antitumour activity and toxicity of the substance and medicinal form of the present preparation of dimethylaminoarglabin hydrochloride was determined according to the commonly used techniques.

Thus, the present method and device enable to produce highly-effective antitumour preparation of the natural origin-arglabin lyophilised possessing high antitumour and immuno-stabilizing activity and relatively low toxicity.

What is claimed is:

1. A method of production of lyophilized hydrochloride 1β, 10β-epoxy-13-dimethyl amino-guaia-3(4)-en-6, 12-olide from endemic plant *Artemsia glabella Kar. et Kir.* including resin extraction from the initial product, its purification from worthless substances, said resin separation into separate components by the method of column chromatography with production of technical arglabin which is further subjected to recrystallisation, amination and hydrochloration with production of aminoarglabin hydrochloride and its further recrystallisation, drying, lyophilisation and high qualitative identification in which:

said amination is carried out by solving crystalline arglabin in alcohol with addition of dimethylamine to the said solution till pH of said solution reaches 12.3–12.4, at the previous stage to extract aminoarglabin hydrochloride containing aminoarglabin, alcohol is distilled and chloroform is filled in, the remaining water is removed, said solution is filtered, said chloroform is evapored and alcohol added, the said solution is barbotaged by chlorine till pH of the solution reaches 5.0–5.5, said alcohol is evapored and ethylacetate is added.

2. The method as claimed in claim 1, wherein said high quality identification of lyophilised arglabin is carried out by means of IR-spectroscopy.

3. A device for the extraction of arglabin lyophilised from natural material consisting of horizontal extractor including cylindrical body divided by partitions with openings into not less than three sections, separation and humidity chamber, the shaft mounted on the same axis with said body, ladles and blade mixers attached to said shaft, and the loader, in which the said extrator is supplied with an additional section with heated walls to remove the extract from waste material and collector of dry waste material, the walls of contact sections are water cooled, the cavities of cooling jackets in the upper parts of the walls, being in contact with vapour-gas medium, and in the lower parts of the walls, being in contact with the extracted mixture, are not open to each other, said system of gas circulation is connected to said extractor cavity, said system for gas supply includes branch pipe connected to the cavity of contact section of the extractor, low temperature condenser and ventilator, the lead screw placed in the separation chamber is connected to the shaft of the extractor, the partition between the separation and the humidity chambers is made with additional opening in its upper part.

4. The device as claimed in claim 3, the cylindrical body of the extractor is inclined.

5. The device as claimed in claim 3, wherein the branch pipe for removing the extract from the separation chamber of the extractor is connected to a filtration centrifuge which is connected with an evaporator and condenser in series.

* * * * *

UNITED STATES PATENT AND TRADEMARK OFFICE
CERTIFICATE OF CORRECTION

Page 1 of 1

PATENT NO.    : 6,242,617 B1
DATED         : June 5, 2001
INVENTOR(S)   : Sergazy Mynzhasarovich Adekenov It is certified that error appears in the above-identified patent and that said Letters Patent is hereby corrected as shown below:

<u>Title page,</u>
Item [76], Inventor replace "(RU)" with -- (KZ) --

<u>Column 12, claim 4,</u>
Line 1, insert -- wherein -- after "in claim 3,"

Signed and Sealed this

Nineteenth Day of March, 2002

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO. : 6,242,617 B1  
DATED : June 5, 2001  
INVENTOR(S) : Sergazy Mynzhasarovich Adekenov Page 1 of 1

It is certified that error appears in the above-identified patent and that said Letters Patent is hereby corrected as shown below:

<u>Title page,</u>
Item [76], Inventor, replace "(RU)" with -- (KZ) --

<u>Column 10,</u>
Line 33, insert -- wherein -- after "in claim 3,"

This certificate supersedes Certificate of Correction issued March 19, 2002.

Signed and Sealed this

Thirtieth Day of April, 2002

Attest:

Attesting Officer

JAMES E. ROGAN
Director of the United States Patent and Trademark Office